(12) United States Patent
Burshtein et al.

(10) Patent No.: US 10,099,068 B2
(45) Date of Patent: Oct. 16, 2018

(54) IMAGING-GUIDED DELIVERY OF X-RAY RADIATION

(71) Applicant: CONVERGENT R.N.R LTD, Tirat Carmel (IL)

(72) Inventors: Zeev Burshtein, Nes-Ziona (IL); Zeev Harel, Kfar Saba (IL); Aharon Bar-David, Nesher (IL); Donald M. Korn, Sanibel Island, FL (US)

(73) Assignee: CONVERGENT R.N.R LTD, Tirat Carmel (IL)

( * ) Notice: Subject to any disclaimer, the term of this patent is extended or adjusted under 35 U.S.C. 154(b) by 0 days.

(21) Appl. No.: 15/414,634

(22) Filed: Jan. 25, 2017

(65) Prior Publication Data
US 2017/0197096 A1    Jul. 13, 2017

Related U.S. Application Data

(60) Division of application No. 14/457,250, filed on Aug. 12, 2014, now Pat. No. 9,586,061, which is a
(Continued)

(51) Int. Cl.
*G01N 23/04* (2018.01)
*A61N 5/10* (2006.01)
(Continued)

(52) U.S. Cl.
CPC .............. *A61N 5/1049* (2013.01); *A61B 6/06* (2013.01); *A61B 6/4021* (2013.01);
(Continued)

(58) Field of Classification Search
CPC .. A61N 5/1049; A61N 5/1084; A61N 5/1065; A61N 2005/1061;
(Continued)

(56) References Cited

U.S. PATENT DOCUMENTS 6,624,431 B1    9/2003   Foster et al.
6,853,702 B2 *  2/2005   Renner ................ A61N 5/1048
                                              378/64
(Continued)

FOREIGN PATENT DOCUMENTS

WO    1997/032454 A1    9/1997
WO    2009/017348 A2    2/2009
(Continued)

OTHER PUBLICATIONS

International Search Report for PCT/IL2013/050121, dated Jan. 23, 2013.
(Continued)

*Primary Examiner* — Courtney Thomas (57) ABSTRACT

An X-ray system comprises: a source of an X-ray diverging beam having a central imaging portion and a peripheral treatment-portion; a lens transforming the peripheral treatment portion of the X-ray beam into a converging beam directed to a target; a shutter located between the X-ray source and the target in the central imaging portion of the X-ray radiation; and a detector of imaging radiation after interaction with the target and to provide imaging information of the target.

14 Claims, 7 Drawing Sheets

Related U.S. Application Data continuation-in-part of application No. PCT/IL2013/050121, filed on Feb. 10, 2013.

(60) Provisional application No. 61/598,035, filed on Feb. 13, 2012.

(51) Int. Cl.
*A61B 6/00* (2006.01)
*A61B 6/06* (2006.01)
*G21K 1/04* (2006.01)
*G21K 1/06* (2006.01)

(52) U.S. Cl.
CPC .......... *A61B 6/4035* (2013.01); *A61N 5/1065* (2013.01); *A61N 5/1084* (2013.01); *G21K 1/04* (2013.01); *G21K 1/065* (2013.01); *A61N 2005/1054* (2013.01); *A61N 2005/1061* (2013.01)

(58) Field of Classification Search
CPC ............. A61N 2005/1054; A61B 6/4021; A61B 6/06; A61B 6/4035; G21K 1/04; G21K 1/065

See application file for complete search history.

(56) References Cited

U.S. PATENT DOCUMENTS

| | | |
|---|---|---|
| 2002/0044626 A1 | 4/2002 | Verman et al. |
| 2003/0142786 A1 | 7/2003 | Houge |
| 2004/0057552 A1* | 3/2004 | Collins ............... A61N 5/1084 378/65 |
| 2006/0193036 A1 | 8/2006 | Suzuki |
| 2009/0190720 A1 | 7/2009 | Windt |
| 2010/0091941 A1 | 4/2010 | Zocchi et al. |
| 2011/0019798 A1 | 1/2011 | Kang et al. |
| 2011/0110499 A1 | 5/2011 | Mitsuda et al. |

FOREIGN PATENT DOCUMENTS

| | | |
|---|---|---|
| WO | 2012/002314 A1 | 1/2012 |
| WO | 2012/012141 A1 | 1/2012 |
| WO | 2013/121418 A1 | 8/2013 |

OTHER PUBLICATIONS

Written Opinion of the International Search Authority for PCT/IL2013/050121, dated Jan. 23, 2013.
International Preliminary Report on Patentability Chapter II for PCT/IL2013/050121, dated Jul. 22, 2014.

* cited by examiner

IMAGING-GUIDED DELIVERY OF X-RAY RADIATION

CROSS-REFERENCE TO RELATED APPLICATIONS

This application is a Divisional application of U.S. patent application Ser. No. 14/457,250, filed 12 Aug. 2014, which is a Continuation-in-Part application of PCT International Application Number PCT/IL2013/050121, filed 10 Feb. 2013, claiming priority from U.S. Provisional Patent Application No. 61/598,035, filed 13 Feb. 2012. All of these applications are hereby incorporated by reference in their entirety.

TECHNICAL FIELD

This patent application relates to X-ray radiation delivery devices and methods, including X-ray radiation therapy devices and methods.

BACKGROUND

X-ray radiation can be used for a wide range of applications, including X-ray therapy and X-ray surgery, various X-ray imaging applications, sensing and detection applications. In these and other applications, the X-ray radiation is directed to a target which can be a tissue or other object at a desired location. It is desirable to properly aim the X-ray beam to a desired point or location on the target in many applications.

SUMMARY

The techniques and devices described here use an X-ray imaging beam to image a target and use the obtained imaging information of the target to control or deliver another X-ray beam onto the desired location of the target.

In one implementation, an X-ray system is provided to include one or more lenses configured to receive a first portion of X-ray radiation from an X-ray source and to direct treatment radiation to converge onto a target; a first shutter located in a path between the X-ray source and the target to receive a second portion of the X-ray radiation from the X-ray source to selectively allow imaging X-ray radiation to reach the target; and a detector configured to detect at least a portion of the imaging radiation after the imaging radiation has interacted with the target to provide imaging information of the target.

In another implementation, a method is provided to include receiving X-ray radiation from an X-ray source at a first shutter located in a path between the X-ray source and a target; using the X-ray source to provide radiation to be directed by one or more lenses as treatment radiation onto the target; controlling an operation of the first shutter to selectively allow the X-ray radiation to reach the target as imaging radiation; receiving at least a portion of the imaging radiation at a detector after the imaging radiation has interacted with the target; and using imaging information of the target from the detector to control a property of the treatment radiation onto the target.

In yet another implementation, a method is provided to include controlling an operation of a first X-ray source in an X-ray system to provide radiation to be directed by one or more lenses as treatment radiation onto a target at one or more converging angles; blocking radiation from the first X-ray source that is not incident upon the one or more lenses from reaching the target; controlling an operation of a second X-ray source in the X-ray system to provide imaging radiation that is incident upon the target; and receiving at least a portion of the imaging radiation at a detector after the imaging radiation has interacted with the target.

These and other implementations of the techniques and devices are described in greater detail in the drawings, the description and the claims.

DETAILED DESCRIPTION

Recent advances in X-ray technology enable effective use of X-ray imaging systems and methodologies in a variety of applications. These applications include, but are not limited to, a variety medical imaging techniques, ranging from plain X-ray imaging of the skeletal system and soft tissue, to fluoroscopy, radiation therapy and radiosurgery. Radiation therapy is commonly applied to cancerous tumors to control or impede cell growth. Ionizing radiation works by damaging the DNA of exposed tissue leading to cellular death. The use of X-ray systems for radiosurgery allows non-invasive treatment of benign and/or malignant tumors enabled by the localized, highly precise concentration of X-rays at the target lesion.

During a radiosurgery session or a radiation therapy treatment it is important to minimize the amount of radiation absorbed by healthy tissue. This requires that the clinicians know precisely where the targeted volume is located before irradiation, and if possible during irradiation. This task is often made more difficult because tumors can change in size over time, especially between radiation courses of many days or weeks. Therefore, often patients are subjected to imaging procedures immediately before radiation sessions so as to determine the size, shape and location of the tumor. However, such procedures, which may include plane radiography using two dimensional imaging sensors, computed tomography (CT), magnetic resonance imaging (MRI) and the like, are costly and can be time consuming. In addition, the target, such as a cancerous tumor, can move and possibly change shape while the radiation therapy is actually taking place. Such a scenario can occur, for example, in a treatment session for prostate cancer, during which the prostate can move because of bladder filling and random movements of the bowels. The movement of a target lesion can also occur due to breathing and heart beating.

The techniques and devices described here are based on imaging-guided delivery of X-ray radiation by using an X-ray imaging beam to image a target and using the obtained imaging information of the target to control and deliver another X-ray beam onto the desired location of the target. For example, the imaging information is used to accurately determine the location, size and other characteristics of a target during, before and after a radiation therapy or radiosurgery session while minimizing the associated complexity, cost and the time involved in acquiring such information.

In this document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

In X-ray therapy, in order to reduce the exposure of healthy tissue during radiation treatments, it is important to determine the exact location, size, shape and other characteristics of a target. To accomplish this task, a relatively new field called Image Guided Radiation Therapy (IGRT) has evolved to assist radiation oncologists to better deliver radiation therapy to the targeted areas. IGRT techniques often involve acquiring imaging data using, MRI, CT, positron emission tomography (PET), and other techniques immediately prior to the radiation therapy session in order to obtain the needed information regarding a target within the patient's body. Monitoring the position of a tumor during a therapy session can also be accomplished using what is often referred to as portal imaging. For example, portal imaging can include placing a two dimensional image sensor behind the patient so that the treating radiation exiting the patient can be imaged along with the tumor. This technique, however, can produce poor results since the tumor may not be differentiated well from its surroundings due to the low contrast of different parts of the body to the very high energy treatment X-rays typical to conventional radiation therapy.

Another approach for obtaining information regarding a target prior to, or during, a course of radiation treatment is to utilize a conventional radiographic X-ray tube operating in the many tens of Kilovolt range and pointed at the tumor in a direction perpendicular to the axis between the irradiating source and the tumor. By aiming this additional X-ray radiation at the tumor region, detecting the radiation that is transmitted through the body using a two dimensional sensor, and rotating the additional X-ray source around the axis to obtain additional images, both plane images and two dimensional reconstructed images similar to a conventional CT image can be attained. Design of such systems, however, requires an extra gantry for the imaging radiation and, therefore, adds substantial cost and bulk to the x-ray system. In addition, such a system can limit the versatility of the irradiation source design.

The disclosed embodiments relate to providing cost effective methods and systems for acquiring accurate information regarding a target prior to, during, or after, a radiation therapy and/or radiosurgery session. A target can include any normal or abnormal target region within a patient's body, including, but not limited to, cancerous and/or benign tumors, lesions and the like. A target can also include both normal and abnormal regions, such as in a scenario where a cancerous tumor and a limited region surrounding the tumor are the target of radian therapy or radiosurgery.

To minimize, or to reduce, irradiating the tissue outside of the target, such as healthy skin or organs that surround a tumor, shaped radiation beams are often focused from several converging angles to intersect at the target. As a result, the target receives a concentrated radiation dosage from the converging beams while the surrounding tissue outside of the focal region receives a much lower radiation dosage. Such systems often utilize optical components with a crystal structure for guiding and/or focusing the X-ray beams based on Bragg or Laue diffraction principals. For example, germanium (Ge) or silicon (Si) curved crystals may be used to deflect diverging radiation from an X-ray source onto a target. Such crystals, which may be singly curved, doubly-curved or be shaped for use with any other technique related to Johansson and Johan geometries, can be utilized in what is called a Rowland circle configuration to provide focusing of the X-ray beams in two or three dimensions, respectively. For instance, a doubly-curved crystal may be used to focus the beams onto a relatively small (e.g., point) target. The crystals can also provide wavelength (or energy) selectivity and, therefore, can be used for filtering purposes to, for example, monochromatize the X-ray radiation.

Figure 1:
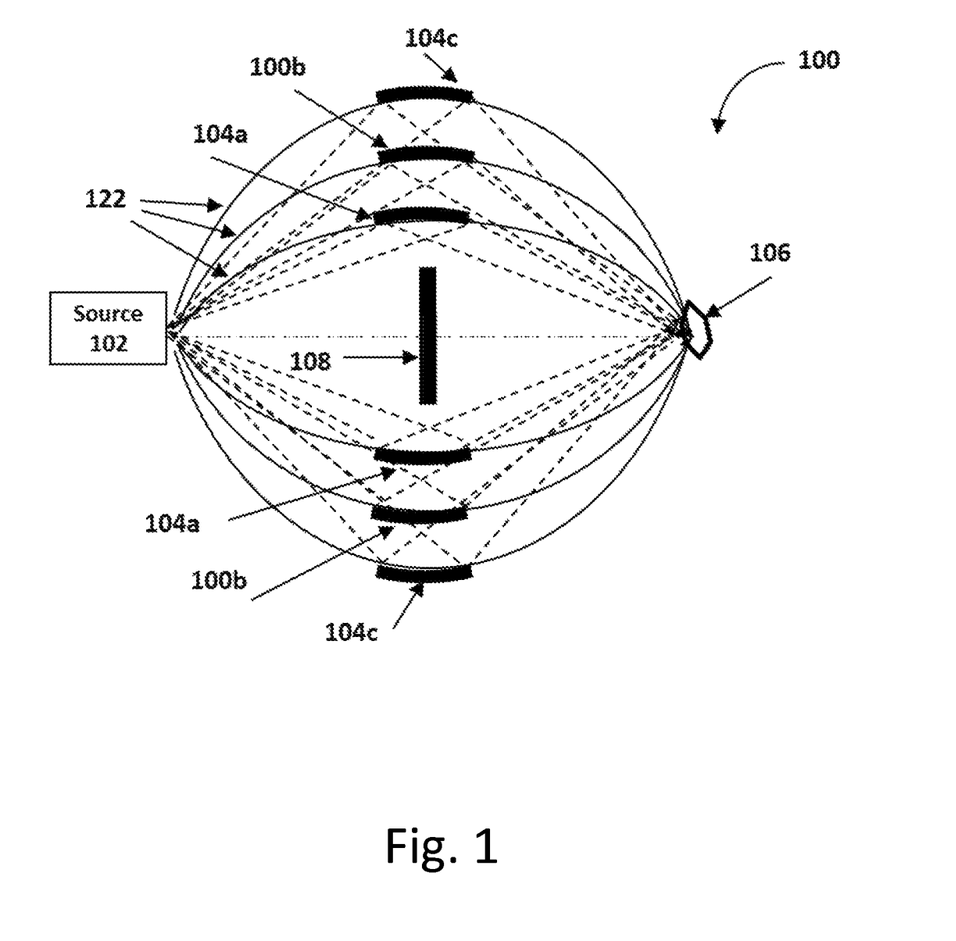
FIG. 1 is a system that is configured to allow treatment of a target using X-ray radiation.

FIG. 1 illustrates an exemplary system 100 that is configured to focus X-ray radiation from a source 102 to a target 106 using a plurality of ring-like lenses 104(a), 104(b) and 104(c). The target 106 can be a tissue of a patient in an X-ray therapy system or other object when the system 100 is used for other applications. Each of the lenses 104(a), 104(b) and 104(c) are positioned on Rowland circles 122 and focus an incident bundle of X-ray beams onto the target 106 at a converging angle.

The term "optical axis" is defined as the line connecting the source 102 with the target 106 passing through the center of the lenses 104(a), 104(b) and 104(c) and shutters 108 and 210.

The lenses 104(a), 104(b) and 104(c) can be constructed in such a way to allow only a limited spectral portion of the incident X-ray radiation to reach the target 106. As such, the X-ray radiation that is directed by the lenses 104(a), 104(b) and 104(c) to the target 106 is sometimes referred to as monochromatic radiation. It should be noted that the term monochromatic in the present context is not necessarily indicative that such radiation only includes one spectral wavelength. But rather the term monochromatic is used to convey that such radiation includes fewer spectral components than unaltered X-ray radiation that is emanating from the X-ray source 102. Since such radiation in the configuration of FIG. 1 is used for radiation treatment, it may also be referred to as the treatment radiation.

The exemplary system 100 of FIG. 1 illustrates only two small portions of each ring-like lens 104(a), 104(b) and 104(c) at the top and bottom of the corresponding Rowland circles 122 as examples. The lenses 104(a), 104(b) and 104(c) are ring-like structures that are appropriately positioned around the axis that connects the source 102 to the target 106. In other exemplary configurations, the number, shape and symmetry characteristics of the lenses 104(a), 104(b) and 104(c) may be altered to accommodate particular applications, cost targets or design goals.

FIG. 1 further illustrates a stop 108 that is placed in the direct path between the source 102 and the target 106 to block X-ray radiation that would otherwise reach the target 106 unimpeded. The radiation that is incident upon the stop 108 may include the full spectral range of the X-ray source 102 (i.e., it is "polychromatic") and may, therefore, harm the patient if not attenuated or blocked by the stop 108.

Figure 2:
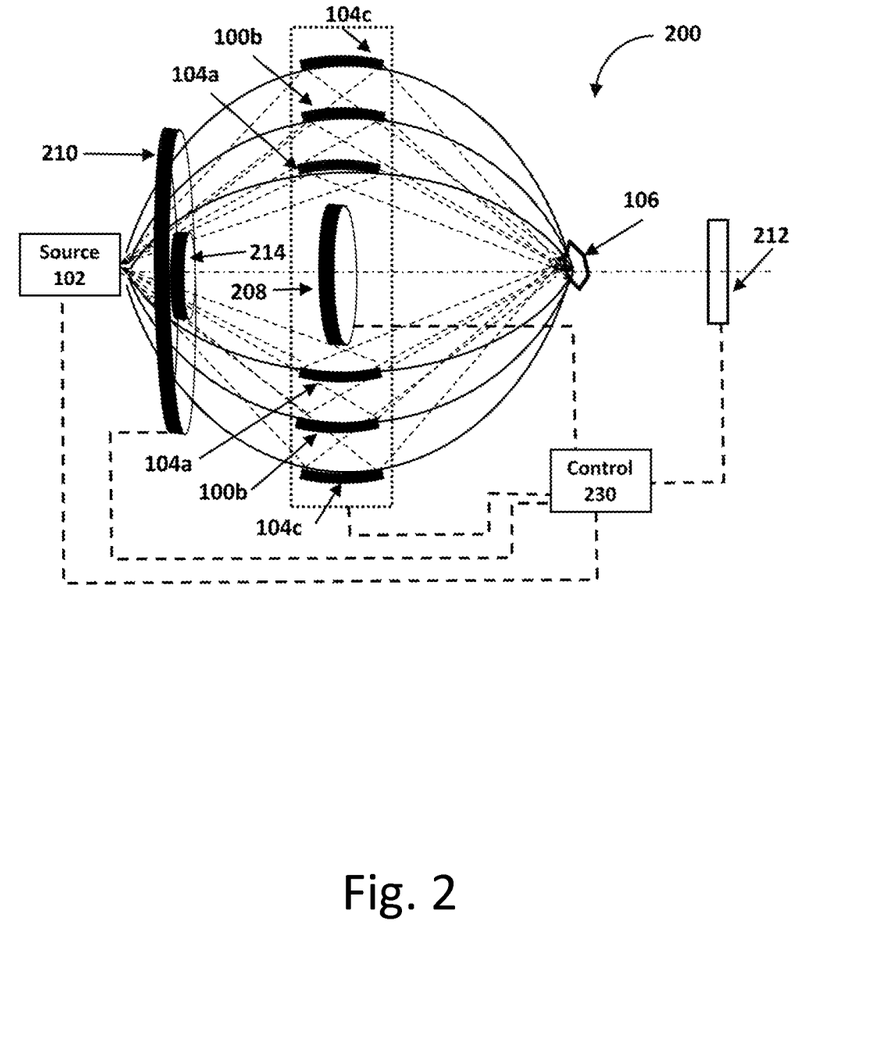
FIG. 2 is a system that is configured to allow treatment, as well as imaging of a target in accordance with an exemplary embodiment.

FIG. 2 illustrates a system 200 that is configured to allow treatment as well as imaging of a target 106 in accordance with an exemplary embodiment. The system 200 enables imaging of the target 106 prior to, during and/or after treatment of the target 106 by allowing at least a portion of the X-ray radiation from the source 102 to directly reach the target 106. The boundaries of the imaging portion of the radiation are shown as 107. Such radiation can be used for imaging purposes and, therefore, is sometimes referred to herein as imaging radiation.

Similar to the system 100 of FIG. 1, the lenses 104(a), 104(b) and 104(c) of FIG. 2 can direct, focus and/or spectrally filter the incident X-ray that is delivered to the target 106 at, for example, high diverging angles. However, in contrast to FIG. 1, X-ray radiation that is not incident on the lenses 104(a), 104(b) and 104(c) is incident upon at least an imaging radiation shutter 208 that is located in the direct path between the source 102 and the target 106. In some example embodiments, the imaging radiation shutter 208, when closed, operates similar to the stop 108 that was described in connection with FIG. 1. As such, in one mode of operation, the imaging radiation shutter 208 can block (or greatly attenuate) the X-ray radiation in the direct path from the source 102 to the target 106.

When the imaging radiation shutter 208 is at least partially open, all or a portion of the X-ray radiation 107 from that is incident upon the imaging radiation shutter 208 can reach the target 106. FIG. 2 also illustrates a detector 212 that is located, for example, behind the patient and can capture at least a portion of the imaging radiation 107 after the imaging radiation has interacted with the target. Such an interaction can include, but is not limited to, reflection, scattering, transmission, and combinations thereof. The detector 212 can include a single detector or a plurality of detector elements that are, for example, arranged to form a detector array. Through the use of at least the imaging radiation shutter 208 and the detector 212, the system 200 of FIG. 2 becomes capable of acquiring images of the target 106 during a treatment session, while the treatment radiation is also being directed to the target 106. In some embodiments, the radiation source 102, the lenses 104(a), 104(b) and 104(c), the shutter 208 and the detector 212 may be rotated around the body (and therefore the target) to irradiate the target 106 from different directions, thus enabling the acquisition of multiple images that can enable reconstruction of, for example, three-dimensional images of the target 106.

In some embodiments, the detector 212 is positioned such that it receives the imaging radiation without receiving appreciable treatment radiation (i.e., radiation from the high divergence beams that are directed to the target 106 by the lenses 104(a), 104(b) and 104(c)). This is illustrated in FIG. 2, where the detector 212 is placed just outside of the path of high divergence beams. In other embodiments, the location and size of the detector 212 can readily adjusted within the system 200. In some embodiments, the treatment radiation may be blocked from reaching the detector 212 by using filters, shutters or other mechanisms. In one particular example, the detector 212 may be implemented as part of a movable mechanism or platform that allows the detector 212 to move inside and outside of the treatment radiation and/or imaging radiation path. Such a movable mechanism may also allow the detector to move within the treatment and/or imaging radiation path to provide images with proper characteristics, such as sharpness, contrast, brightness, and the like.

In some embodiments, the imaging radiation is filtered to modify the spectral content and/or intensity of the X-ray radiation that is incident upon the target 106 so as to protect the non-target regions from harmful radiation. Moreover, filtering of the imaging radiation 107 may be adjusted to provide optimal contrast, brightness, sharpness and other characteristics of the acquired images. Filtering of the imaging radiation can be carried out using filters that are constructed from, for example, metal sheets that are placed in the imaging radiation path. In some example embodiments, such filters constitute separate components from the imaging radiation shutter 208. In some embodiments, however, the filters may be implemented as part of the imaging radiation shutter 208.

According to some embodiments, a treatment radiation shutter 210 may be placed in the path between the X-ray source 102 and the lenses 104(a), 104(b) and 104(c) so as to block or attenuate the radiation that would normally reach the lenses 104(a), 104(b) and 104(c). A variety of shutter designs for both the imaging and treatment radiation can be used, including designs that are typically used in photographic cameras. In FIG. 2, the treatment radiation shutter 210 is illustrated as having a hollow central portion 214 to allow the imaging radiation 107 from the source 102 to propagate towards the target 106. The treatment radiation shutter 210 and the imaging radiation shutter 208 may be controlled independently from one another to enable simultaneous or time-multiplexed operations of the two shutters. For example, in one mode of operation, the treatment radiation shutter 210 is configured to block the treatment radiation, while the imaging radiation shutter 208 is configured to allow at least a portion of the imaging radiation 107 to reach the target 106. This exemplary mode of operation can, for example, be utilized prior to or after a treatment session, as well as during a treatment session when the treatment radiation is momentarily turned off.

In another mode of operation, the treatment radiation shutter 210 is configured to allow the treatment radiation to reach the lenses 104(a), 104(b) and 104(c), while the imaging radiation shutter 208 is configured to block the imaging radiation 107. This exemplary mode of operation can, for example, be utilized during a treatment session when acquiring images of the target 106 is not needed. In another mode of operation, the treatment radiation shutter 210 is configured to allow the treatment radiation to reach the lenses 104(a), 104(b) and 104(c), while the imaging radiation shutter 208 is also configured to allow at least a portion of the imaging radiation 107 to reach the target 106. This exemplary mode of operation can, for example, be utilized during a treatment session to allow simultaneous treatment and imaging of the target.

In another mode of operation, both the treatment radiation shutter 210 and imaging radiation shutter 208 may be configured to block the respective radiations. This exemplary mode of operation can, for example, be used when the X-ray system is turned off or is temporarily disabled to allow, for example, movement of the x-ray tube and/or the whole system configuration to a new position. By controlling the operations of the treatment radiation shutter 210 and the imaging radiation shutter 208, different modes of operations can be combined to, for example allow the treatment and imaging radiations to reach the target 106 in a time-multiplexed fashion in accordance with a desired duty cycle. The control signals that are provided to the treatment radiation shutter 210 and the imaging radiation shutter 208 can be controlled through additional components (not shown) that can be implemented as hardware, software, firmware or combinations thereof.

In some implementations, a system control module 230 is provided in the system 200 to control the imaging-guided delivery of the treatment radiation onto the target 106. The control module 230 can be in communications with the detector 212 enabling the movement of the detector 212 (if needed), to receive imaging information of the target based on the received radiation at the detector 212, and to control the operations of the imaging radiation shutter 208, the treatment radiation shutter 210, and the X-ray source 102. The control module 230 can be used to automated controls of the source 102, the shutters 210 and 208 based on the imaging information from the detector 212. The control module 230 can also be used to control the lenses 104(a), 104(b) and 104(c), e.g., the positions or orientations of such lenses, to adjust the treatment radiation from the lenses 104(a), 104(b) and 104(c) onto the target based on the imaging information from the detector 212. This adjustment can be in the position, spectral contents, intensity, or focusing of the converged treatment radiation on the target 106.

Figure 3:
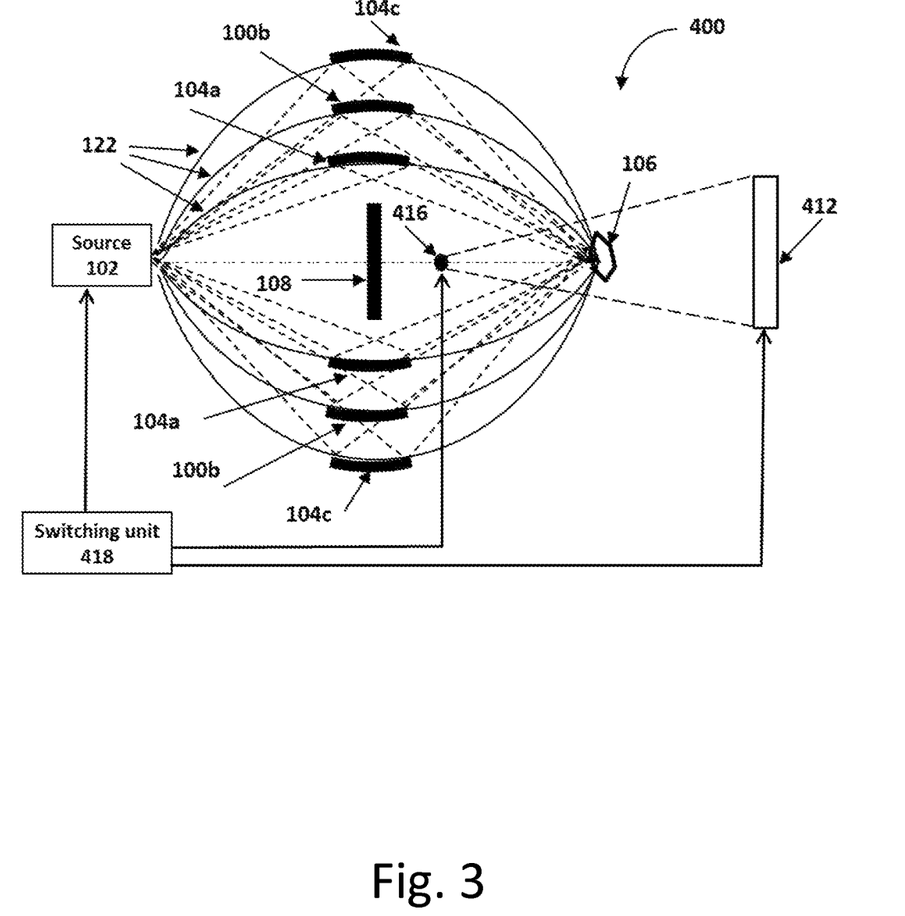
FIG. 3 is a system that is configured to allow treatment, as well as imaging of a target in accordance with another exemplary embodiment.

FIG. 3 illustrates a system 300 that is configured to allow treatment, as well as imaging of a target 106 in accordance with another exemplary embodiment. The exemplary system 300 of FIG. 3 includes similar components as the exemplary system 200 of FIG. 2, except for the treatment radiation shutter 310 that is located in the path between the lenses 104(a), 104(b) and 104(c) and the target 106. Such a configuration enables the use of a thinner and lighter treatment radiation shutter 310 since such a shutter operates on monochromatic X-ray radiation. Compared to the treatment radiation shutter 210 of FIG. 2, the hollow central portion 314 of the treatment radiation shutter 310, as well as the portions of the shutter 210 that modulate that treatment radiation, may need to be modified in size to enable for the propagation of sufficient imaging and treatment radiation through the treatment radiation shutter. Numeral 307 refers to boundaries of the imaging portion of the radiation. Moreover, compared to the treatment radiation shutter 210 of FIG. 2, the choice of placement of the treatment radiation shutter 310 may be limited to only a fraction of the distance between the lenses 104(a), 104(b) and 104(c) and the target 106 since the last portion of that distance is likely within the body of the patient. The detector 312 of FIG. 3 is also depicted as having a somewhat different size and location compared to its counterpart in FIG. 2. This change is merely done to illustrate that different detectors with different sizes and at different locations can be implemented as part of the disclosed embodiments.

In some embodiments, the imaging radiation shutter and the treatment radiation shutter may be incorporated as part of a single composite shutter. In such a configuration, the central portion of the composite shutter operates as an imaging radiation shutter (with or without filtering capability), whereas the remaining portions of the composite shutter operate as a treatment radiation shutter. As discussed above in connection with FIGS. 2 and 3, the two shutters can be controlled independently from one another to enable simultaneous or time-multiplexed gating and/or modulation of the imaging and treatment radiations.

The above described systems of the exemplary embodiments can be constructed in a very cost effective manner since they require only a single radiation source for both treatment and imaging purposes. Therefore, by adding one or more shutters, one or more filters (optional), an imaging detector and the associated electronic circuitry, an X-ray treatment system can be utilized to also produce accurate data describing the location and the size of a target. Moreover, in the above described systems of the exemplary embodiments in FIGS. 2 and 3, the imaging axis and treatment axis are substantially the same. The alignment of the treatment radiation and the imaging radiation simplifies the calibration (or mapping) of the position of the treatment radiation relative to the imaging radiation.

In some embodiments an additional shutter 315 blocks the treatment X-rays and/or scattered X-rays from reaching the detector 312 such that only the imaging X-rays are collected by the detector.

In some embodiments, the energy of the X-ray source, which can be used for imaging and treatment purposes, is below 1 Mega electron volt (Mev). In one particular example, the spectral range of the treatment radiation can be selected to be in the range of several tens of electron volts. Such a spectral range is also suitable for achieving high contrast imaging, which allows proper differentiation of different body parts. By selecting the imaging radiation to be somewhat centered in this spectral range, the choice and thickness of metal shutters and filters becomes quite cost effective, as is the mechanism for opening and closing the shutters. For example, the shutters can be produced using relatively thin sheets of material with properly selected atomic number Z values so as to provide the needed absorption of the respective radiation. This is in stark contrast to the expensive shuttering mechanisms needed in conventional radiation therapy equipment, such as the very thick metal components needed in Multi Leaf Collimators (MLC) to stop the typical high energy treatment beams in linear accelerators.

In some exemplary embodiments, the X-ray treatment/imaging system is designed to be able to move the focal spot of the X-ray tube toward or away from the target. Such a capability provides varying degrees of magnification of the area of interest when the X-ray treatment/imaging system is used in imaging only mode. In addition, such a capability provides variability in selecting the size of the imaged area.

Figure 4:
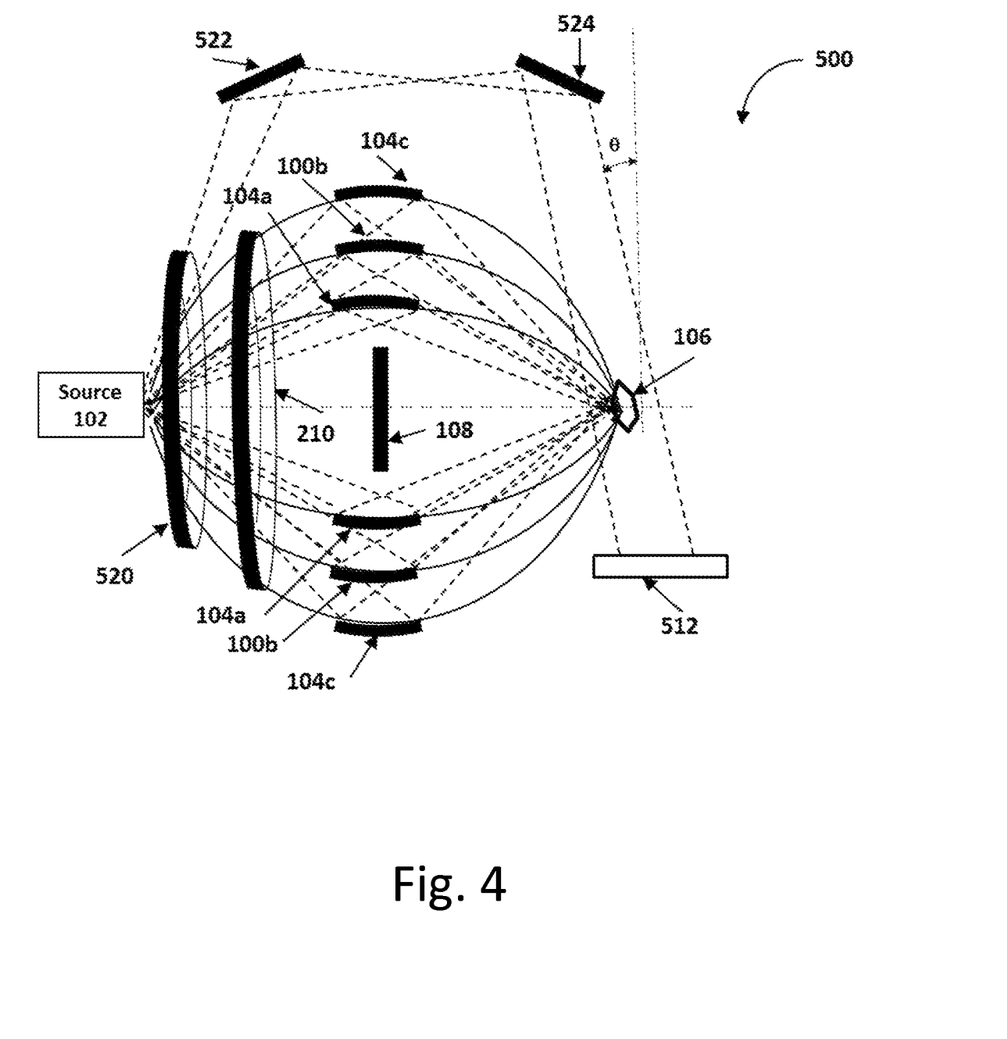
FIG. 4 is a system that is configured to allow treatment, as well as imaging of a target in accordance with another exemplary embodiment.

FIG. 4 illustrates a system 500 that is configured to allow treatment, as well as imaging of a target 106 in accordance with another exemplary embodiment. The exemplary system 500 includes some components that are similar to those illustrated in FIG. 2, including the lenses 104(a), 104(b) and 104(c), the first radiation source 102, the stop 108, the treatment radiation shutter 210 and the target 106. The exemplary system 500 of FIG. 4 further includes an imaging system that guides the radiation outside the optical axis via path 507 reaching target 106 at an angle relative to the optical axis. The exemplary system 500 of FIG. 4 further includes an imaging radiation shutter 520 that is configured to control the imaging radiation 507 that is incident upon the target 106 through a plurality of reflectors 522, 524. In one example embodiment, the reflectors 522, 524 are double reflection reflectors. The detector 512 captures at least a portion of the imaging radiation after it has interacted with the target 106. The imaging radiation shutter 520 does not affect the radiation that is directed to the one or more lenses 104(a), 104(b) and 104(c) by, for example, including a hollow central portion. In contrast to FIG. 2, the imaging radiation of the exemplary system 500 of FIG. 5 does not traverse a direct path between the X-ray source 102 and the target 106. But, as illustrated in FIG. 4, the imaging radiation reaches the target 106 after reflections from the reflectors 522, 524. The reflectors 522 and 524 that are depicted in the exemplary system 500 of FIG. 4 can have the suitable geometry that is needed to allow proper reflection of the imaging radiation onto the target 106. For example, the reflectors 522, 524 can be concave, convex or flat (or combinations thereof) crystal reflectors.

The exemplary system 500 of FIG. 4 can further include a filter in the imaging radiation path that operates to limit at least one of the intensity and/or spectral content of the radiation that irradiates the target. Similar to the operations of the exemplary systems in FIGS. 2 and 3, the first and second shutters can be controlled to enable simultaneous or time-multiplexed irradiation of the target 106 with the treatment and imaging radiation. In the exemplary system 500 of FIG. 4, the reflectors 522, 524 and the detector 512 form one reflector-detector set. In some embodiments, several reflector-detector sets are provided to enable the acquisition of multiple images from multiple angles. Alternatively, or additionally, the one or more reflector-detector sets can be rotated around the target in order to enable the acquisition of multiple images for construction of, for example, two and three-dimensional images by, for example, using Tomo Synthesis, simple CT techniques or other techniques. In some embodiments, where complete rotations around the target are not possible, only rotations within a particular angular cone (illustrated in FIG. 4, by the way of example, as a cone having an angle $\Theta$) are carried out to acquire images of the target 106.

The exemplary embodiments that are shown in FIGS. 1 to 4 illustrate X-ray treatment/imaging systems with components that operate based on Bragg diffraction principles. However, it is understood that the disclosed embodiments can additionally, or alternatively, utilize components that operate based on Laue diffraction principles. As such, filtering, focusing and guiding of the X-ray radiation can be carried out using transmissive and/or reflective components.

Moreover, at least some of the imaging techniques and systems that are described herein can be used in non-X-ray treatment systems, such as in proton therapy or other radiation therapy systems. As such, the imaging techniques and components that are described in the present application may be used to enable imaging of a target before, during and after a non-X-ray treatment session.

Figure 5:
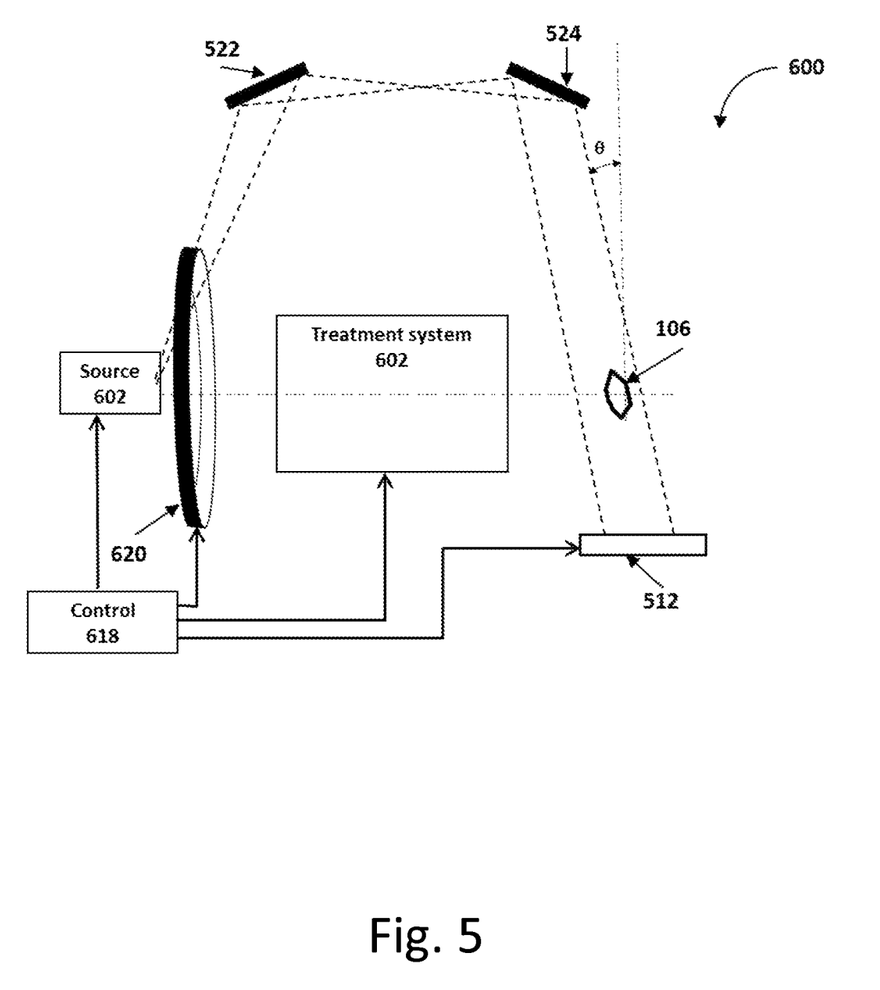
FIG. 5 is a system that is configured to allow treatment, as well as imaging of a target in accordance with another exemplary embodiment.

For example, FIG. 5 illustrates a system 600 that is configured to allow treatment, as well as imaging of a target 106 in accordance with another exemplary embodiment. Similar to the configuration of FIG. 4, the radiation from the source 602 is reflected by the reflectors 522, 524 and reaches the target 106 via path 507 as imaging radiation. At least a portion of the imaging radiation is received at the detector 512 after interacting with the target 106. The treatment system 602 can be a non-X-ray treatment system such as a proton therapy system. The radiation from the source 602 may be modulated and/or turned on/off using an imaging radiation shutter 618.

Additionally, or alternatively, the operation of the source 602 may be controlled through a control module 618. In example embodiments that utilized the imaging radiation shutter 618, the operation of the imaging radiation shutter 620 can also be controlled by the control module 618. The control module 618 may also control the operation of the detector 512 and, optionally, the treatment system 602. For example, the control module 618 may sent or receive synchronization information and signals to/from the treatment system 602. The imaging radiation 507 may be optionally filtered to produce the desired intensity and/or spectral content of the imaging radiation that is received at the target 106.

Figure 6:
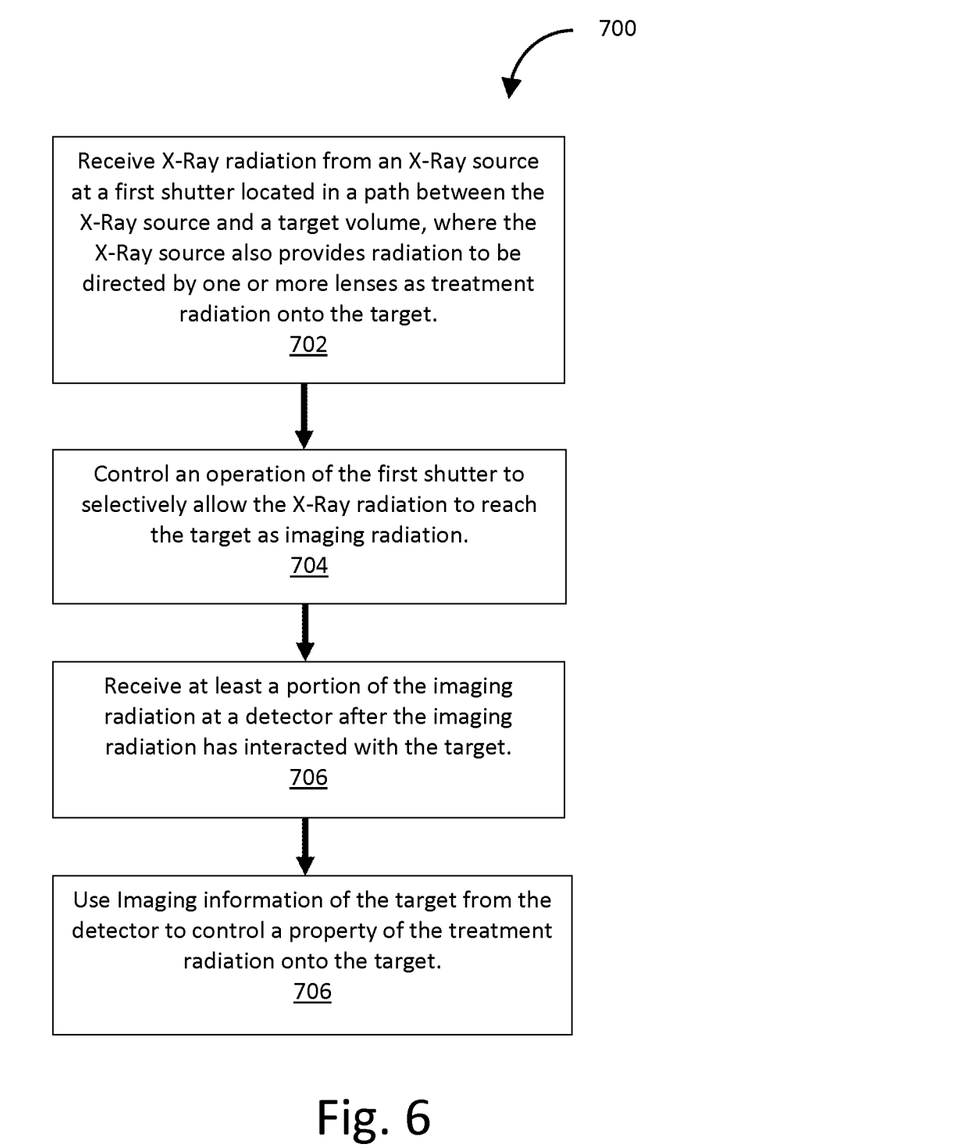
FIG. 6 is a set of operations that allows treatment, as well as imaging of a target in accordance with an exemplary embodiment.

FIG. 6 illustrates a set of operations 700 that can be carried out to allow treatment, as well as imaging of a target in accordance with an exemplary embodiment. At 702, X-ray radiation from an X-ray source at a first shutter (i.e., the imaging radiation shutter) is received. The first shutter is located in a path between the X-ray source and the target, and the X-ray source also provides radiation to be directed by one or more lenses as treatment radiation onto a target at, for example, one or more converging angles. At 704, the operation of the first shutter is controlled to selectively allow the X-ray radiation to reach the target as imaging radiation. At 706, at least a portion of the imaging radiation is received at a detector, after the imaging radiation has interacted with the target. At 706, the imaging information of the target from the detector is used to control a property of the treatment radiation onto the target. In some embodiments, the operations 700 can further include (not shown) controlling a second shutter (i.e., treatment radiation shutter) to selectively allow the treatment radiation to reach the target.

Figure 7:
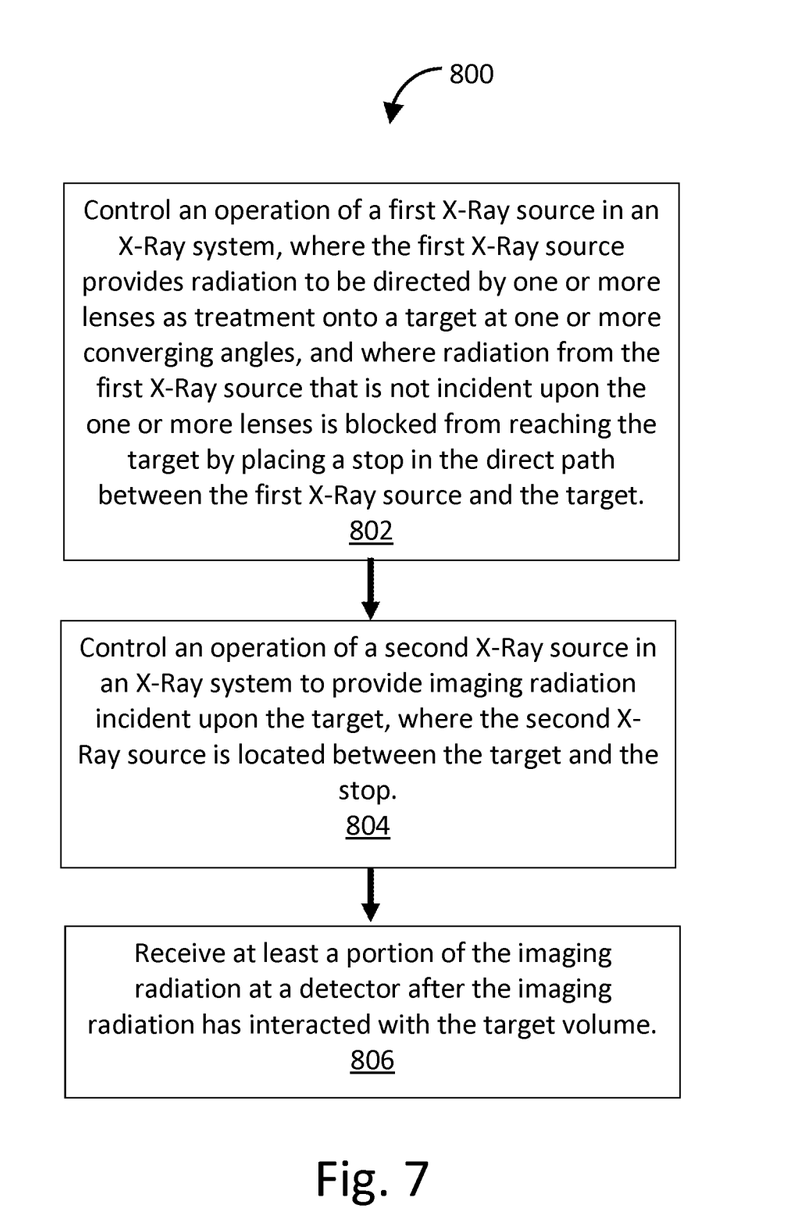
FIG. 7 is a set of operations that allows treatment, as well as imaging of a target in accordance with another exemplary embodiment.

FIG. 7 illustrates a set of operations 800 that can be carried out to allow treatment, as well as imaging of a target in accordance with another exemplary embodiment. At 802, operation of the first X-ray source in an X-ray system is controlled. The first X-ray source provides radiation to be directed by one or more lenses as treatment radiation onto a target at one or more converging angles. The radiation from the first X-ray source that is not incident upon the one or more lenses is blocked from reaching the target by placing a stop in the direct path between the first X-ray source and the target. At 804, an operation of a second X-ray source in the X-ray system is controlled to provide imaging radiation that is incident upon the target. The second X-ray source is located between the target and the stop. At 806, at least a portion of the imaging radiation is received at the detector, after the imaging radiation has interacted with the target.

The operation of the X-ray treatment/imaging systems that are described in the present application can require synchronous and/or asynchronous control of the treatment and imaging components, including but not limited to control of the X-ray source(s), filters, shutters, imaging detectors, focusing and targeting components, and the like. To this end, specific hardware, software and/or firmware components can be developed to provide the needed timing synchronization and control of the various components of the X-ray systems. For example, some or all of the needed operations can be implemented using a processor, a memory unit, and an interface that are communicatively connected to each other. In particular, the memory can be in communication with the processor, and at least one communication unit enables the exchange of data and information, directly or indirectly, through a communication link with other entities, devices, user interfaces, databases and networks. The communication unit can, for example, provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information.

Moreover, at least some of the embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

The invention claimed is:

1. An X-ray system for imaging a target and treating thereof, comprising:
   a. a source providing an X-ray diverging beam having a central imaging portion directly illuminating the target and neighboring tissues and a peripheral treatment portion transformable into a converging beam;
   b. at least one lens transforming the peripheral treatment portion of the X-ray beam into the converging beam directed to the target;
   c. a first shutter located between the X-ray source and the target in the central imaging portion of the X-ray radiation; the first shutter being selectively openable such that central imaging portion of X-ray beam directly reaches the target; and
   d. a detector configured to detect at least a central imaging portion of the radiation directly illuminating the target after interaction thereof with the target and to provide imaging information of the target.

2. The X-ray system of claim 1, wherein the first shutter is configured to allow the imaging radiation to reach the target when the following conditions are alternatively true:
   a. the treatment radiation is not irradiating the target; and
   b. the treatment radiation is irradiating the target.

3. The X-ray system of claim 1, further comprising a filter located in the path between the X-ray source and the target, wherein the filter is configured to limit at least one of a spectral content and intensity of the imaging radiation that reaches the target.

4. The X-ray system of claim 3, wherein the filter is configured to be adjusted to allow achieving desired characteristics for images of the target acquired by the detector.

5. The X-ray system of claim 1, further comprising a second shutter being openable such that the treatment portion of X-ray beam reaches to the target.

6. The X-ray system of claim 5, wherein the second shutter is located between the X-ray source and the one or more lenses.

7. The X-ray system of claim 5, wherein the second shutter is located between the one or more lenses and the target.

8. The X-ray system of claim 5, wherein the first shutter and the second shutter are realized as an integral shutter; the first shutter and the second shutter are configured to enable at least one of the following conditions to occur:
   a. the target is irradiated by both the treatment radiation and the imaging radiation;
   b. the target is irradiated by the treatment radiation but not by the imaging radiation;
   c. the target is irradiated by the imaging radiation but not the treatment radiation; and
   d. the target is irradiated by both the treatment radiation and the imaging radiation in a time-multiplexed manner.

9. The X-ray system of claim 1, wherein at least one of the first shutter, the detector and the one or more lenses are configured to be rotated around the target, thereby enabling irradiation of the target with the treatment and/or imaging radiation from a plurality of angles.

10. The X-ray system of claim 5, wherein the detector is implemented as part of movable mechanism that allows the detector to move outside of, or within, imaging and/or treatment radiation paths.

11. The X-ray system of claim 5, wherein the first shutter is located in a direct patch between the X-ray source and the target volume.

12. The X-ray system of claim 5, wherein a third shutter is located in front of said detector.

13. The X-ray system of claim 5, wherein at least one of the shutters is actuated.

14. An X-ray system for imaging a target and treating thereof, comprising:
   a. a source providing an X-ray diverging beam having an imaging portion and a treatment portion angularly separated there between;
   b. at least one lens transforming the treatment portion of the X-ray diverging beam into a converging beam directed to a target;
   d. at least one reflector in an off-axis position directing the imaging portion of the X-ray diverging beam angularly to an optical axis to the target;
   e. a stop blocking an axially propagating portion of the X-ray diverging beam source within an internal space of at least one lens from reaching the target;
   f. a detector configured to detect the imaging portion of the X-ray diverging beam-after interaction thereof with the target and to provide imaging information of the target; the detector and at least one reflector are rotatable around the target such that the target is imaged at a plurality of angles.

* * * * *